United States Patent [19]

Panzera et al.

[11] Patent Number: 5,775,912
[45] Date of Patent: Jul. 7, 1998

[54] METHOD OF PRODUCING A DENTAL RESTORATION USING CAD/CAM

[75] Inventors: Carlino Panzera, Belle Mead; Richard A. Brightly, Westwood; Lisa M. DiMeglio, Monmouth Junction; Jana Pruden, Belle Mead, all of N.J.

[73] Assignee: American Thermocraft Corporation, Somerset, N.J.

[21] Appl. No.: 699,149

[22] Filed: Aug. 16, 1996

[51] Int. Cl.⁶ .................................................. A61C 5/10
[52] U.S. Cl. .................................... 433/223; 433/212.1
[58] Field of Search ................................ 433/213, 223, 433/229, 212.1; 364/474.03, 474.05, 474.39

[56] References Cited

U.S. PATENT DOCUMENTS

| | | |
|---|---|---|
| 4,575,805 | 3/1986 | Moermann . |
| 4,663,720 | 5/1987 | Duret et al. . |
| 4,671,770 | 6/1987 | Bell et al. .............................. 433/223 |
| 4,798,536 | 1/1989 | Katz ..................................... 433/212.1 |
| 4,937,928 | 7/1990 | Van Der Zel . |
| 5,106,303 | 4/1992 | Oden et al. ............................. 433/223 |
| 5,180,427 | 1/1993 | Prasad et al. ........................... 106/35 |
| 5,378,154 | 1/1995 | Van Der Zel ........................... 433/223 |

OTHER PUBLICATIONS (1) IntraTech brochure "Introducing the 90–minute crown and the IntraTech PRO–CAM", 1995 copyright IntraTech Dental Products, Inc. Design.

*Primary Examiner*—Ralph Lewis
*Attorney, Agent, or Firm*—Cummings & Lockwood

[57] ABSTRACT

A method of making a dental porcelain restoration comprises providing a soft-sintered dental porcelain pellet; milling the soft-sintered pellet under the control of a CAD/CAM system to provide a tooth structure; investing the tooth structure with an investment refractory material to provide an invested tooth structure; fusing the invested tooth structure; and removing the investment refractory material from the fused tooth structure to provide the dental restoration.

12 Claims, No Drawings

METHOD OF PRODUCING A DENTAL RESTORATION USING CAD/CAM

FIELD OF THE INVENTION

This invention relates to a method of producing a dental restoration and, more particularly, to a method which employs CAD/CAM.

BACKGROUND OF THE INVENTION

Dental porcelains are typically comprised of a fine powder of "glass-like" particles, e.g., Optec™ porcelain powder sold by Jeneric/Pentron Incorporated (Wallingford, Conn.). To fabricate a dental restoration, water or some suitable liquid is added to the powder. A wet, sandy mix is created which can be formed into desired shapes and then fused by heat to produce a solid substance similar to glass. In this manner, porcelain may be enameled to metal or simply baked into a solid mass of pure porcelain. Restorations are usually fabricated on a replica or die of the prepared tooth. Materials may be added to the porcelain powders which improve color and strength.

Another method of fabricating dental restorations is hot-pressing (high temperature injection molding). This technique is initiated by creating the restoration in wax. The wax pattern is lifted from the die and invested or surrounded by a mix of "plaster-like" material which is allowed to harden. A channel or opening leads from the outer surface of the investment into the wax pattern. Wax is eliminated from the investment during a burnout procedure. The dental porcelain, provided in powder or pellet form, is placed in a special hot press and is melted and forced under pressure into the opening of the investment. Examples of porcelain pellets include soft-sintered OPC® pellets sold by Jeneric/Pentron Incorporated (Wallingford, Conn.) and fully fused Empress® porcelain pellets sold by Ivoclar AG (Schaan, Liechtenstein). The melted material fills the void created by the wax pattern. After cooling, the hardened ceramic is broken out of the investment. Where desired, color can be baked onto the surface of the restoration to simulate tooth color.

Yet another method of fabricating dental restorations involves the computer-aided design, i.e., CAD/CAM, technique. In such a method, a 3-dimensional photo is taken of the stump of tooth over which a dental restoration is to be placed and of the teeth surrounding the stump. This photo is digitized and supplied to the CAD/CAM system, displaying the 3-dimensional picture on a viewing screen. The dental practitioner selects the most suitable tooth form from a plurality of tooth forms stored in the CAD/CAM system and projects the image of the selected tooth form over the stump until an optimum positioning and fit of the dental restoration is obtained. The digital data concerning the dental restoration thus formed are supplied to a numerically controlled milling machine operating in three dimensions, which precisely cuts a blank, i.e., a solid piece of metal or fully fused dental porcelain, on the basis of the digital data to provide the dental restoration.

It has been observed that use of fully fused dental porcelain pellets wear down cutting tools and significantly slow down the process of dental restoration fabrication. The milling of fully fused dental porcelains results in excessive chipping and flaking, thus affecting the precision of the milling operation and, ultimately, the fit between the restoration and the patient's natural teeth.

It is an object of the present invention to provide a CAD/CAM method of making a dental restoration which significantly reduces the wear of cutting tools on milling machines controlled by CAD/CAM and improves the fit between the dental restoration and the patient's natural teeth.

SUMMARY OF THE INVENTION

In accordance with these and other objects of the present invention, a method of making a dental restoration is provided which comprises:

providing a soft-sintered dental porcelain pellet;

milling the soft-sintered pellet under the control of a CAD/CAM system to provide a tooth structure;

investing the tooth structure with an investment refractory material to provide an invested tooth structure;

fusing the invested tooth structure; and removing the investment refractory material from the fused tooth structure to provide the dental restoration.

The phrase "soft-sintered dental porcelain pellet" as utilized herein shall be understood to refer to a pellet that is formed by compressing at ambient temperature dental porcelain powder into a pellet (possessing any desired shape and configuration) and subsequently heating the pellet to a temperature which is sufficiently below the fusion temperature of the dental porcelain such that the density of the resulting soft-sintered pellet is less than about 85 percent, typically less than about 75 percent, of the theoretical density of the pellet. Such soft-sintered pellets possess a white, chalky appearance and are somewhat porous. This situation is to be contrasted with the case where the pellets are heated to a temperature which is at or close to the fusion temperature of the dental porcelain such that the density of the resulting sintered pellet is greater than about 90 percent of the theoretical density of the pellet. Such fully fused pellets possess a translucent, glossy appearance and exhibit very little, if any, porosity.

The term "tooth structure" as utilized herein includes milled soft-sintered pellets possessing shapes which replicate natural teeth or are intended to be in association with natural teeth.

One of the surprising advantages of the present invention is that dental restorations produced via the method of this invention exhibit significantly higher strength characteristics compared to dental restorations fabricated from fully fused pellets instead of soft-sintered pellets.

DESCRIPTION OF THE PREFERRED EMBODIMENTS

CAD/CAM techniques and/or systems which can be utilized in the practice of this invention are not particularly limited and can include those described, for example, in U.S. Pat. Nos. 4,575,805 and 4,663,720, the contents of which are incorporated by reference herein. An example of a commercially available CAD/CAM system which can advantageously be utilized in the practice of this invention is the PRO-CAM™ system available from IntraTech Dental Products (Dallas, Tex.).

The dental porcelain used to fabricate the soft-sintered pellet utilized herein is likewise not particularly limited. Preferably, the dental porcelain is high strength Optec™ porcelain powder sold by Jeneric/Pentron Incorporated (Wallingford, Conn.). Optec™ porcelain powder possesses a fusion temperature of about 1027° C. To fabricate Optec™ porcelain powder into a soft-sintered pellet, a suitable amount of powder is placed in a suitable pressing device, e.g., a Carver laboratory press, and compressed under pressure, e.g., 5000 psi, into a pellet at ambient temperature.

Thereafter, the pellet is heated, e.g., in a conventional dental porcelain oven, to a temperature ranging from about 650° to about 925° C. to soft-sinter the pellet. The resulting soft-sintered pellet possesses a density which is less than about 85, typically less than about 75, percent of the theoretical density of the pellet (as measured by Archimedes method).

Alternatively and more preferably, the soft-sintered pellet is a high strength OPC® porcelain pellet sold by Jeneric/Pentron Incorporated (Wallingford, Conn.). OPC® porcelain pellets are sold in the soft-sintered form and thus can be readily used in the practice of this invention. OPC® porcelain pellets possess a fusion temperature of about 1150° C.

After the soft-sintered pellet has been milled under the control of a CAD/CAM system to provide a desired tooth structure, the resulting tooth structure is invested with an investment refractory material. The investment refractory material selected depends on the composition of the soft-sintered pellet. It is well known in the art that the investment refractory material should not change dimension when heated to high temperatures. Preferably, the refractory investment material possesses a coefficient of thermal expansion which is about $0.5 \times 10^{-6}/°C$. less than that of the soft-sintered dental porcelain pellet. When Optec™ porcelain is employed in the method herein, it is preferred in the practice of the method herein to employ Optec™ Instant Refractory Material sold by Jeneric/Pentron Incorporated (Wallingford, Conn.) as the investment refractory material. When OPC® soft-sintered porcelain pellets are employed, it is preferred to employ OPC® Instant Refractory Material sold by Jeneric/Pentron Incorporated (Wallingford, Conn.) as the investment refractory material.

The invested tooth structure is then fused by heating the pellet in a vacuum furnace to the fusion temperature of the soft-sintered pellet as is well known in the art.

After the fused tooth structure has cooled, the investment material is removed from the fused tooth structure to provide a dental restoration which will precisely fit the tooth being restored and the surrounding teeth. Of course, it will be understood that veneering porcelain and/or stains may be subsequently placed on top of the outer surface of the resulting dental restoration utilizing techniques which are well known in the art.

The following example illustrates the practice of the present invention.

EXAMPLE

An OPC® soft-sintered dental porcelain pellet (available from Jeneric/Pentron, Inc., Wallingford, Conn.) is machined into a tooth structure in partial shape or final shape using a PRO-CAM™ (trademark of IntraTech Dental Products Inc.) computer-assisted milling machine (available from Jeneric/Pentron Incorporated, Wallingford, Conn.). The tooth structure is then invested with an investment refractory material (sold by Jeneric/Pentron Incorporated under the tradename Optec™ Instant Refractory material) which does not change dimension when exposed to high temperature. The invested tooth structure is fused by placing the sample in a conventional dental porcelain furnace at an initial temperature of 650° C. and increasing the temperature to 1150° C. at a heat-up rate of 55° C./min. The tooth structure is held at 1150° C. for 30 seconds. The fully fused tooth structure is cleaned of the investment to provide a dental restoration which is prepared to receive a suitable veneering porcelain. The fully fused dental restoration has sufficient viscosity when re-heated to the maturing temperature of the veneering porcelain such that it does not lose its shape during the firing cycle of the veneering porcelain. At maturity, the veneering porcelain forms a tight impervious surface necessary in the oral environment. Optimal™ porcelain (Jeneric/Pentron, Inc., Wallingford, Conn.) is provided as a powder and is mixed with water or other suitable liquid to form a slurry. The slurry is applied to the dental restoration in accordance with well-known techniques and fused in a conventional dental porcelain furnace by heating the coated dental restoration from about 650° C. to about 970° C. at a heat-up rate of about 55° C./min. and holding at about 970° C. for 30 seconds. The resultant coated dental porcelain restoration fits back into the original model.

Further variations and modifications of the present invention will become apparent to those skilled in the art from the foregoing and are intended to be encompassed by the claims appended hereto.

What is claimed is:

1. A method of making a dental restoration which comprises:

providing a soft-sintered dental porcelain pellet;

milling the soft-sintered dental porcelain pellet under the control of a CAD/CAM system to provide a tooth structure;

investing the tooth structure with an investment refractory material to provide an invested tooth structure;

fusing the invested tooth structure; and removing the investment refractory material from the fused tooth structure to provide the dental restoration.

2. The method of claim 1 wherein the soft-sintered dental porcelain pellet possesses a density which is less than about 85 percent of the theoretical density of the pellet.

3. The method of claim 1 wherein the soft-sintered pellet is formed by compressing at ambient temperature dental porcelain powder into a pellet and subsequently heating the pellet to a temperature below the fusion temperature of the dental porcelain to provide a pellet possessing a density which is less than about 85 percent of the theoretical density.

4. The method of claim 3, wherein the fusion temperature is about 1027° C.

5. The method of claim 4, wherein the temperature below the fusion temperature ranges from about 650° C. to about 925° C.

6. The method of claim 3, wherein the dental porcelain powder is compressed at about 5000 psi.

7. The method of claim 1 wherein the soft-sintered dental porcelain pellet possesses a density which is less than about 75 percent of the theoretical density of the pellet.

8. The method of claim 1 wherein the soft-sintered pellet is formed by compressing at ambient temperature dental porcelain powder into a pellet and subsequently heating the pellet to a temperature below the fusion temperature of the dental porcelain to provide a pellet possessing a density which is less than about 75 percent of the theoretical density.

9. The method of claim 8, wherein the fusion temperature is about 1027° C.

10. The method of claim 9, wherein the temperature below the fusion temperature ranges from about 650° C. to about 925° C.

11. The method of claim 8, wherein the dental porcelain powder is compressed at about 5000 psi.

12. The method of claim 1, wherein the soft-sintered pellet has a fusion temperature of about 1150° C.

\* \* \* \* \*